(12) United States Patent
Senaratne et al.

(10) Patent No.: US 11,773,416 B2
(45) Date of Patent: **\*Oct. 3, 2023**

(54) CARBON DIOXIDE BIOCONVERSION PROCESS

(71) Applicant: Jupeng Bio, Inc., League City, TX (US)

(72) Inventors: Ryan H Senaratne, Fayetteville, AR (US); Abel J Price, Fayetteville, AR (US); Brandon L Beard, Fayetteville, AR (US)

( \* ) Notice: Subject to any disclaimer, the term of this patent is extended or adjusted under 35 U.S.C. 154(b) by 701 days.

This patent is subject to a terminal disclaimer.

(21) Appl. No.: 16/530,481

(22) Filed: Aug. 2, 2019

(65) Prior Publication Data

US 2020/0308611 A1    Oct. 1, 2020

Related U.S. Application Data

(60) Provisional application No. 62/741,871, filed on Oct. 5, 2018, provisional application No. 62/741,797, filed on Oct. 5, 2018, provisional application No. 62/716,053, filed on Aug. 8, 2018, provisional application No. 62/716,083, filed on Aug. 8, 2018, provisional application No. 62/716,071, filed on Aug. 8, 2018.

(51) Int. Cl.
  *C12P 7/54*  (2006.01)
  *C12P 7/52*  (2006.01)

(52) U.S. Cl.
  CPC .. *C12P 7/54* (2013.01); *C12P 7/52* (2013.01)

(58) Field of Classification Search
  CPC ...... C12P 7/52; C12P 7/54; C12P 7/40; Y02E 50/10
  See application file for complete search history.

(56) References Cited

U.S. PATENT DOCUMENTS

| | | | |
|---|---|---|---|
| 7,285,402 B2 | 10/2007 | Gaddy et al. | |
| 8,293,509 B2 | 10/2012 | Simpson et al. | |
| 10,036,045 B2 | 7/2018 | Muller et al. | |
| 2010/0227377 A1\* | 9/2010 | Adams ..................... | C12P 7/08 435/252.1 |
| 2014/0080195 A1\* | 3/2014 | Senaratne ................ | C12Q 3/00 435/163 |
| 2016/0040192 A1 | 2/2016 | Scott et al. | |
| 2016/0251683 A1 | 9/2016 | Tracy et al. | |
| 2019/0153488 A1 | 5/2019 | Stephanopoulous et al. | |
| 2019/0211302 A1 | 7/2019 | Bruno-Barcena et al. | |

FOREIGN PATENT DOCUMENTS

| | | |
|---|---|---|
| KR | 1020180077972 A | 7/2018 |
| WO | 2014202965 A1 | 12/2014 |
| WO | 2016070160 A1 | 5/2016 |
| WO | 2017205363 A1 | 11/2017 |
| WO | 2017210296 A1 | 12/2017 |

OTHER PUBLICATIONS

Lehtinen et al., "Production of Alkanes from CO2 by Engineered Bacteria", Biotechnol Biofuels (2018) 11:228.
Mayer et al., "Carbon Monoxide Conversion with Clostridium aceticum", Biotechnology and Bioengineering 2018:115:2740-2750.
Mourato et al., "A Continuous System for Biocatalytic Hydrogenation CO2 to Formate", Bioresource Technology 255 (2017):149-156.
Muller, "Energy Conservation in Acetogenic Bacteria", Applied and Environmental Microbiology, vol. 69, No. 11, pp. 6345-6353, Nov. 2003.
Muller, "New Horizons in Acetogenic Conversion of One-Carbon Substrates and Biological Hydrogen Storage", Trends in Biotechnology XP-0027940231 (2019).
Poehlein et al., "An Ancient Pathway Combining Carbon Dioxide Fixation with the Generation and Utilization of a Sodium Ion Gradient for ATP Synthesis", PLoS ONE 7(3): e33439. doi:10.1371/journal.pone.0033439, Mar. 29, 2012.
Rowaihi et al., "A Two-Stage Biological Gas to Liquid Transfer Process to Convert Carbon Dioxide into Bioplastic", Bioresource Technology Reports 1 (2018) 61-68.
Takora et al., "Using Gas Mixtures of CO, CO2 and H2 as Microbial Substrates: the Do's and Don'ts of Successful Technology Transfer from Laboratory to Production Scale", Microbial Biotechnology 11, 506-625 (2018).
Valgepea et al. "H2 Drives Metabolic Rearrangements in Gas-Fermenting Clostridium autoethanogenum", Biotechnol. Biofuels (2018) 11:55.
Weuster-Botz, "Chemicals from CO2: Hydrogenotrophic Protection of Acetate with Acetobacterium woodii", Dechema, 2013, https://dechema.de/events_media/Veranstaltungen/2013/Irsee_Analytics_2013/Session+Heterogene+biotechnische+Systeme-p-5242.pdf.
Yu et al., "Efficient Reduction of CO2 by the Molybdenum-Containing Formate Dehydrogenase from Cupriavidus necator (*Ralstonia eutropha*)", J. Biol. Chem. (2017) 292(41) 16872-16879.
Acharya et al., "Ethanol Production by Syngas Fermentation in a Continuous Stirred Tank Bioreactor Using Clostridium jungdahlii", Biofuels, 10:2, 221-237, May 16, 2017.

(Continued)

*Primary Examiner* — Renee Claytor
*Assistant Examiner* — Tiffany M Gough
(74) *Attorney, Agent, or Firm* — Mengqi Zheng; James Krueger (57) ABSTRACT

A $CO_2$, bioconversion process includes providing a $CO_2$ containing substrate to a bioreactor, the $CO_2$ containing substrate including about 5 to about 90 mole % $CO_2$; and fermenting the $CO_2$ containing substrate with an acetogenic bacteria carrying a sodium translocating ATPase. The medium including less than about 0.01 grams per liter yeast extract, less than about 0.01 grams per liter carbohydrate, a sodium ion concentration provided by a sodium ion feed rate of about 290 to about 8750 µg/gram of cells/minute, and a pH of about 4 to about 6.9.

14 Claims, 8 Drawing Sheets

(56) References Cited

OTHER PUBLICATIONS

Balch et al., "Acetobacterium, a New Genus of Hydrogen-Oxidizing, Carbon Dioxice-Reducing, Anaerobic Bacteria", International Journal of Systematic Baceteriology, vol. 27, No. 4, pp. 355-361, Oct. 1977.
Bertsch et al., "CO Metabolism in the Acetogen Acetobacterium woodii", Appl. Enviorn. Microbiol. 81:5949-5956, Jun. 19, 2015.
Buschhorn et al., "Production and Utilization of Ethanol by the Homoacetogen Acetobacterium woodii", Applied and Environmental Microbiology, vol. 55, No. 7, pp. 1835-1840, Jul. 1989.
Ceccaldi et al., "The Hydrogen Dependent CO2 Reductase: The First Completely CO tolerant FEFE-hydrogenase", Energy Environ. Sci. 2017, 10, 503, Oct. 24, 2016.
Groher et al., "Comparative Reaction Engineering Analysis of different Acetogenic Bacteria for Gas Fermentation", Journal of Biotechnology 228(2016): 82-89.
Haas et al., "Technical Photosynthesis Involving CO2 Electrolysis and Fermentation", Nature Catalysis, vol. 1, pp. 32-33, Jan. 2018.
Humphreys et al. "Advances in Metabolic Engineering in the Microbial Production of Fuels and Chemicals from C1 Gas", Current Opinion in Biotechnology 2018, 50:174-181.
Imkamp et al., "Chemisomotic Energy Conservation with Na+ as the Coupling Ion during Hydrogen-Dependent Caffeate Reduction by Acetobacterium woodii", Journal of Bacteriology, vol. 184, No. 7, pp. 1947-1951, Apr. 2002.
Jones et al., "CO2 Fixation by Anaerobic Non-Photosynthetic Mixotrophy for Improved Carbon Conversion", Nature Communications 7:1280, DOI: 10.1038/ncomms1800, Sep. 30, 2016.

\* cited by examiner

CARBON DIOXIDE BIOCONVERSION PROCESS

This application claims the benefit of U.S. Provisional Application Nos. 62/716,083, filed Aug. 8, 2018, 62/716,071, filed Aug. 8, 2018, 62/716,053, filed Aug. 8, 2018, 62/741,871, filed Oct. 5, 2018, and 62/741,797, filed Oct. 5, 2018, all of which are incorporated in their entirety herein by reference.

A process is provided for bioconversion of carbon dioxide. More specifically, the process includes providing a carbon dioxide containing gaseous stream to acetogenic bacteria. The process provides for high levels of carbon dioxide conversions and utilization of hydrogen.

BACKGROUND

Carbon dioxide generation occurs from natural processes as well as industrial processes that include combustion of fossil fuels such as coal, oil and natural gas. Due in part to industrial processes, atmospheric carbon dioxide concentration continues to increase. These increases in carbon dioxide concentration may contribute to atmospheric changes which result in climate change and global warming. Carbon dioxide is difficult to utilize in biological processes because of its highly oxidized state.

In addition to carbon dioxide, many industrial processes also result in production of hydrogen. Hydrogen has a high level of reducing potential. However, hydrogen is difficult to store and utilize due to its very flammable nature.

In view of the large amount of carbon dioxide generated, there is a need for a bacterial fermentation system that can reduce a carbon dioxide footprint. Further, there is a need for a fermentation system that can effectively utilize the reducing potential of hydrogen.

SUMMARY

A process includes providing a gaseous substrate to a bioreactor. The gaseous substrate includes $CO_2$, and contains about 5 to about 90 mole % $CO_2$. The process includes providing acetogenic bacteria to the bioreactor; providing sodium ions to the bioreactor through one or more sodium ion sources; and fermenting the gaseous substrate with the acetogenic bacteria in a fermentation broth comprising the acetogenic bacteria and the one or more sodium ion sources to produce one or more organic acids. The acetogenic bacteria include a sodium translocating ATPase that is active during fermentation in the bioreactor. The fermentation broth includes less than about 0.01 grams per liter yeast extract, less than about 0.01 grams per liter carbohydrate and a sodium ion concentration provided by a sodium feed rate of about 290 to about 8750 µg/g of cells/minute. The fermentation broth is maintained at a pH in a range of about 4 to about 6.9.

In another aspect, a process providing a gaseous substrate to a bioreactor. The gaseous substrate includes $CO_2$ and $H_2$ and contains about 5 to about 90 mole % $CO_2$. The process includes providing acetogenic bacteria to the bioreactor; providing sodium ions to the bioreactor through one or more sodium ion sources; and fermenting the gaseous substrate with the acetogenic bacteria in a fermentation broth comprising the acetogenic bacteria and the one or more sodium ion sources to produce one or more organic acids. The acetogenic bacteria includes a sodium translocating ATPase that is active during fermentation in the bioreactor. The fermentation broth includes less than about 0.01 grams per liter yeast extract, less than about 0.1 grams per liter carbohydrate and a sodium ion concentration provided by a sodium feed rate of about 290 to about 8750 µg/g of cells/minute. The fermentation broth is maintained at a pH in a range of about 4 to about 6.9.

A composition includes one or more of a source of $NH_4^+$, P, K, Fe, Ni, Co, Se, Zn, W, or Mg; about 875 to about 35,000 mg/L of a sodium ion source; about 0.009 to about 0.397 mg/L of a Mo source. The composition includes less than about 0.01 grams per liter yeast extract, and less than about 0.01 grams per liter carbohydrates. The composition has a pH of about 4 to about 6.9.

BRIEF DESCRIPTION OF FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

The following description is not to be taken in a limiting sense, but is made merely for the purpose of describing the general principles of exemplary embodiments. The scope of the disclosure should be determined with reference to the claims.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "fermenter" includes a fermentation device/bioreactor consisting of one or more vessels and/or towers or piping arrangements, which includes a batch reactor, semi-batch reactor, continuous reactor, continuous stirred tank reactor (CSTR), bubble column reactor, external circulation loop reactor, internal circulation loop reactor, immobilized cell reactor (ICR), trickle bed reactor (TBR), moving bed biofilm reactor (MBBR), gas lift reactor, membrane reactor such as hollow fibre membrane bioreactor (HFMBR), static mixer, gas lift fermentor, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of $CO_2$, to acetic acid.

The term "cell density" means mass of microorganism cells per unit volume of fermentation broth, for example, grams/liter.

The term "specific $CO_2$ uptake" means an amount of $CO_2$ in mmoles consumed by unit mass of microorganism cells (g) per unit time in minutes, i.e. mmole/gram/minute.

As used herein, productivity is expressed as STY. In this aspect, alcohol productivity may be expressed as STY (space time yield expressed as g ethanol/(L·day) or (g acetic acid/(L·day).

$CO_2$-Containing Gaseous Substrate

In one aspect, the process includes providing a $CO_2$-containing gaseous substrate to a bioreactor. A $CO_2$-containing substrate may include any gas that includes $CO_2$. In this aspect, a $CO_2$-containing gas may include industrial gases, fermentor gas streams including for example, fermentor off-gases and mixtures thereof. In a related aspect, the $CO_2$-containing substrate may include hydrogen or it may be blended with a hydrogen source to provide desired levels and ratios of $H_2$ to $CO_2$.

Industrial gases: In one aspect, the process includes providing a $CO_2$-containing gaseous substrate to a bioreactor where the $CO_2$-containing gaseous substrate is generated from industrial gases. Some examples of industrial gases include steel mill gas, industrial flue gas and incinerator exhaust gas. Examples of industrial gases include gases produced during ferrous metal products manufacturing, non-ferrous products manufacturing, petroleum refining processes, gasification of coal, gasification of biomass, electric power production, carbon black production, ammonia production, methanol production and coke manufacturing. Sources of hydrogen may include fossil fuels, steam reforming, oxidation of methane, coal gasification, and water electrolysis.

Depending on the composition of the gaseous $CO_2$-containing substrate, it may also be desirable to treat it to remove any undesired impurities, such as dust particles before introducing it to the fermentation. For example, the gaseous substrate may be filtered or scrubbed using known methods. Further, depending on the composition of the gaseous $CO_2$-containing substrate, the process may include adjusting the $CO_2$-containing substrate to increase or decrease concentrations of $CO_2$ and/or $H_2$ to fall within desired ranges.

Fermentor Gas Streams: In one aspect, the process includes providing a $CO_2$-containing substrate to a bioreactor where the $CO_2$-containing substrate is a fermentor gas stream. Some examples of fermentor gas streams include fermentor off-gas generated in the fermentation of syngas. Some examples of syngas fermentation are described in U.S. Pat. No. 7,285,402, filed Jul. 23, 2001, which is incorporated herein by reference.

In one aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. The fermentation of CO-containing gas may result in $CO_2$, in fermentor off-gas. As such, the processes represent effective processes for capturing carbon that would otherwise be exhausted into the environment. In this aspect, the off-gas from the fermentation of CO-containing gas may include about 0.5 mole % to about 50 mole % CO.

Blending of gas streams: According to particular aspects, streams from two or more sources can be combined and/or blended to produce a desirable and/or optimized substrate stream. For example, a stream comprising a high concentration of $CO_2$, such as the exhaust from a steel mill, can be combined with a stream comprising high concentrations of $H_2$, such as the off-gas from a steel mill coke oven.

Depending on the composition of the $CO_2$-containing substrate, the $CO_2$-containing substrate may be provided directly to a fermentation process or may be further modified to include an appropriate $H_2$ to $CO_2$ molar ratio. The $CO_2$-containing substrate may include from about 5 to about 90 mole % $CO_2$ and from about 5 to about 90 mole % $H_2$. In one aspect, the $CO_2$ containing gas stream includes about 5 to about 66.6% $CO_2$.

In another aspect, the $CO_2$-containing substrate may include from about 0 mole % to about 50 mole % CO, in another aspect, about 0.5 mole % CO to about 50 mole % CO, in another aspect, about 0.5 mole % CO to about 5 mole % CO, and in another aspect, about 2 mole % CO to about 5 mole % CO.

In one aspect, the acetogenic bacteria will have a molar ratio of consumption of $H_2$ to $CO_2$ at a ratio of about 4:1 to about 1:2. Hence, any substrate gas provided to the bioreactor that includes $H_2$ and $CO_2$ can be utilized. However, optimal levels of substrate gas provided to the bioreactor will have a ratio of $H_2$ to $CO_2$ of about 4:1 to about 1:1, in another aspect, about 2:1, and in another aspect, about 3.5:1 to about 1.5:1.

Bioreactor Design and Operation

Descriptions of fermentor designs are described in U.S. Ser. No. 13/471,827 and Ser. No. 13/471,858, both filed May 15, 2012, and U.S. Ser. No. 13/473,167, filed May 16, 2012, all of which are incorporated herein by reference.

The fermentation should desirably be carried out under appropriate conditions for the desired fermentation to occur (e.g. $CO_2$-to-acetic acid). Reaction conditions to considered include pressure, temperature, gas flow rate, liquid flow rate, medium pH, agitation rate (if using a stirred tank reactor), inoculum level, and maximum acetic acid concentration to avoid product inhibition. In this aspect, the process includes reaction conditions in the following ranges:

Pressure: about 0 to about 500 psi;
Temperature: about 30° C. to about 42° C.;
Medium pH: about 4 to about 6.9;
Agitation rate: about 100 to about 2000 rpm;
Nutrient supply as described herein.

Acetoenic Bacteria

In one aspect, the microorganisms utilized include acetogenic bacteria that include a sodium pump which may also be described as sodium-translocating ATPases (for membrane bioenergetics). Sodium-translocating ATPase are described in Muller, "Energy Conservation in Acetogenic Bacteria", Appl. Environ. Microbial. November 2003, vol. 69, no. 11, pp. 6345-6353, which is incorporated herein by reference. The term sodium translocating ATPase may be used interchangeably with sodium dependent ATPase. Acetogens that include a sodium-translocating ATPase require about 500 ppm NaCl in their growth medium for growth. To determine if an acetogen includes a sodium-translocating ATPase, the acetogen is inoculated into a serum bottles containing about 30 to about 50 ml of growth medium with about 0 to about 2000 ppm NaCl. Growth at NaCl concentrations of about 500 ppm or more means that the acetogen includes a sodium-translocating ATPase.

In this aspect, suitable microorganisms include *Acetobacterium* bacteria, *Acetogenium kivui*, *Acetoanaerobium noterae*, *Acetobaeterium woodii*, *Alkalibaculum bacchi* CP11 (ATCC BAA-1772), *Moorella thermoacetica*, *Morella thermoautotrophica*, *Ruminococcus productus*, and combinations thereof. In another aspect, the microorganism is *Acetobacterium woodii*.

Medium Compositions and Control of Medium Feed Rates

In accordance with one aspect, the fermentation process is started by addition of a suitable medium to the reactor vessel. The liquid contained in the reactor vessel may include any type of suitable nutrient medium or fermentation medium. The nutrient medium will include vitamins and minerals effective for permitting growth of the microorganism being used. Sterilization may not always be required.

Concentrations of various medium components are as follows:

| Element | Concentration mg/L | Feed Rate µg/gram cells/min |
|---|---|---|
| $NH_4^+$ | 82-3280 | 20.5-820 |
| Fe | 0.85-34 | 0.28-8.5 |
| Ni | 0.07-2.81 | 0.023-0.702 |
| Co | 0.037-1.49 | 0.012-0.373 |
| Se | 0.027-1.1 | 0.009-0.274 |
| Zn | 0.59-23.8 | 0.198-5.95 |
| Mo | 0.003-0.397 | 0.003-0.1 |
| chelator | 2.5-100 | 0.83-25 |
| W | 0.8-32.1 | 0.26-8.03 |
| K | 98-3933 | 32.77-983.35 |
| Mg | 0.71-28.69 | 0.23-7.18 |
| Na | 875-35000 | 290-8750 |
| S | 15-625 | 2.08-62.5 |
| P | 20-805 | 6.7-201.3 |
| d-biotin | 0.016-0.64 | 0.005-0.16 |
| thiamine HCl | 0.04-1.6 | 0.01-0.4 |
| calcium-D-pantothenate | 0.02-0.81 | 0.006-0.202 |

Vitamins solution contains d-biotin, thiamine HCl, and calcium-D-pantothenate.

0.5 M NaOH was used to keep the pH around 5.55. The approximate usage of NaOH per gram of cells per hour was 0.1 to 0.4 ml/min per gram of cells.

Process operation maintains a pH in a range of about 4 to about 6.9, in another aspect, about 5 to about 6.5, in another aspect about 5.1 to about 6, and in another aspect, about 5.2 to about 6. The medium includes less than about 0.01 g/L yeast extract and less than about 0.01 g/L carbohydrates.

The composition also includes a sodium ion concentration of about 40 to about 500 mmol per liter, in another aspect, about 40 to about 250 mmol per liter and in another aspect, a sodium ion concentration of about 50 to about 200 mmol per liter. In one aspect, the sodium ion concentration is about 500 ppm to about 8000 ppm, in another aspect, about 1000 ppm to about 7000 ppm, in another aspect, about 3000 ppm to about 6000 ppm, in another aspect, about 2000 to about 5000 ppm Na, and in another aspect, about 3000 to about 4000 ppm Na. The sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

The composition includes a source of molybdenum. In this aspect the molybdenum concentration is about 3.97 µg/L to about 396.5 µg/L, and in another aspect, about 7.93 µg/L to about 198.25 µg/L. Sources of molybdenum include $Na_2MoO_4$, $CaMoO_4$, $FeMoO_4$ and mixtures thereof.

The composition may also include a complexing agent. In this aspect, a complexing agent may be included in the composition when the composition has a pH of about 5.2 or greater. The complexing agent may include ethylenediaminetetraacetic acid (EDTA), ethylenediamine diacetic acid (EDDA), ethylenediamine disuccinic acid (EDDS) and mixtures thereof.

The composition may include one or more of a source of $NH_4^+$, K, Fe, Ni, Co, Se, Zn, or Mg. Sources of each of these elements may be as follows.

$NH_4^+$: The nitrogen may be provided from a nitrogen source selected from the group consisting of ammonium hydroxide, ammonium chloride, ammonium phosphate, ammonium sulfate, ammonium nitrate, and mixtures thereof.

P: The phosphorous may be provided from a phosphorous source selected from the group consisting of phosphoric acid, ammonium phosphate, potassium phosphate, and mixtures thereof.

K: The potassium may be provided from a potassium source selected from the group consisting of potassium chloride, potassium phosphate, potassium nitrate, potassium sulfate, and mixtures thereof.

Fe: The iron may be provided from an iron source selected from the group consisting of ferrous chloride, ferrous sulfate, and mixtures thereof.

Ni: The nickel may be provided from a nickel source selected from the group consisting of nickel chloride, nickel sulfate, nickel nitrate, and mixtures thereof.

Co: The cobalt may be provided from a cobalt source selected from the group consisting of cobalt chloride, cobalt fluoride, cobalt bromide, cobalt iodide, and mixtures thereof.

Se: The selenium may be provided from $Na_2SeO_3$, $C_3H_6NO_2Se$, and mixtures thereof.

Zn: The zinc may be provided from $ZnSO_4$.

W: The tungsten may be provided from a tungsten source selected from the group consisting of sodium tungstate, calcium tungstate, potassium tungstate, and mixtures thereof.

Me: The magnesium may be provided from a magnesium source selected from the group consisting of magnesium chloride, magnesium sulfate, magnesium phosphate, and mixtures thereof.

S: The composition may also include sulfur. The sulfur may be provided from a sulfur source selected from the group consisting of cysteine, sodium sulfide, NaHS, $NaH_2S$ and mixtures thereof.

Fermentation Startup and Post-Startup

Startup: Upon inoculation, an initial feed gas supply rate is established effective for supplying the initial population of microorganisms. Effluent gas is analyzed to determine the content, of the effluent gas. Results of gas analysis are used to control feed gas rates. In this aspect, the process provides a minimal cell density of about 0.1 grams per liter. In another aspect, the process provides a calculated $CO_2$ concentration (mmol/min) to initial cell density ratio of about 0.05 to about 0.5, and in another aspect, about 0.01 to about 1.

In one aspect, nutrients may be added to the culture to increase cell growth rates. Suitable nutrients may include non-carbohydrate fractions of yeast extract.

Post-startup: Upon reaching desired levels, liquid phase and cellular material is withdrawn from the reactor and replenished with medium. The fermentation process is effective for increasing cell density as compared to a starting cell density. In this aspect, the process provides an average cell density of about 2 to about 50 grams/liter, in another aspect, about 2 to about 30 grams/liter, in another aspect, about 2 to about 20 grams/liter; in another aspect, about 2 to about 10 grams/liter, and in another aspect, about 2 to about 6 grams/liter.

Production of Organic Acid: In another aspect, the process provides a source of C1 to C10 organic acids. In this aspect, the process may include obtaining acid product or products from the fermentation liquid broth. In this aspect, provides a specific organic acid productivity of about 0.2 to about 50 grams organic acid/day/g cells, in another aspect, about 0.2 to about 20 grams organic acid/day/g cells, in another aspect, about 10 to about 50 grams organic acid/day/g cells, in another aspect, about 14 to about 30 grams organic acid/day/g cells, in another aspect, about 2 to about 20 grams organic acid/day/g cells and in another aspect, about 15 to about 25 grams organic acid/day/g cells. In one aspect, the organic acid is acetic acid or butyric acid, or a mixture of both.

Conversions of $CO_2$ and $H_2$: The process is effective for providing a $CO_2$ uptake of about 0.05 to about 1.5 mmol $CO_2$/minute/gram dry cells, an $H_2$ uptake of about 0.08 to about 1.5 mmol $H_2$/minute/gram dry cells. The process is effective for providing about 25 to about 100% conversion of $CO_2$, in another aspect, about 50 to about 100% conversion of $CO_2$, and in another aspect, about 75 to about 100% conversion of $CO_2$. In another aspect, the process is effective for providing about 25 to about 100% conversion of $H_2$, in another aspect, about 50 to about 100% conversion of $H_2$, and in another aspect, about 75 to about 100% conversion of $H_2$.

Figure 1:
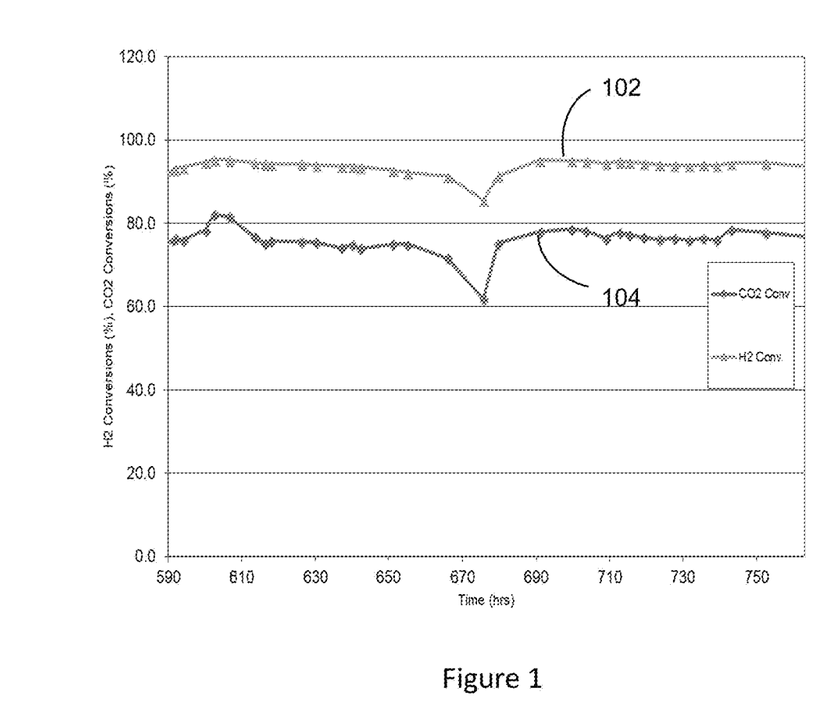
FIG. 1 shows a graph of $CO_2$ conversion and $H_2$ conversion by *Acetobacterium woodii* in a bioreactor.
Figure 2:
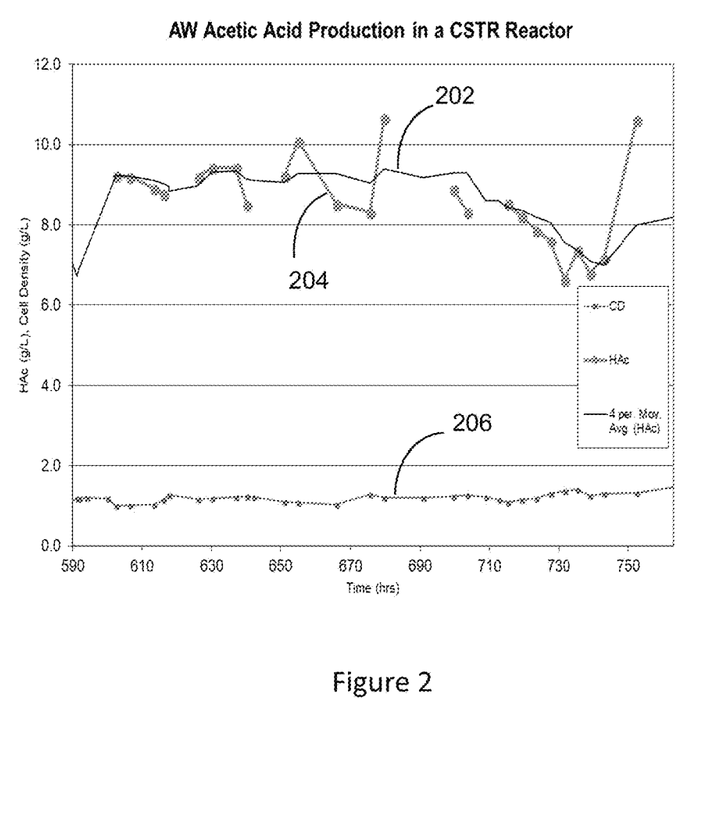
FIG. 2 illustrates acetic acid production by *Acetobacterium woodii*.

FIG. 1 shows a graph of $CO_2$ conversion 104 and $H_2$ conversion 102 by *Acetobacterium woodii*. A graphical illustration of acetic acid production 204 and its moving average 202, and cell density 206 versus time is shown in FIG. 2.

EXAMPLES

Example 1: Preparation of *Acetobacterium woodii*

An initial lyophilized pellet of *Acetobacterium woodii* was obtained from German culture collection DSMZ, strain ID DSM-1030. Culture was initially revived from lyophilized pellet using rich, medium (fructose and yeast extract). An adaptation method was used to remove fructose from serum bottle medium where concentration of fructose in growth medium was stepped down 75%, 50%, 10%. Growth rate and gas usage was used as an indicator of adaptation. (approximately 5 weeks). Preliminary pH adaptation work in serum bottles reduced required pH from 7.4 to 6.0 (3 weeks). At this point, culture was amplified and inoculated into a reactor. In a reactor culture was further adapted to grow in lower pH of 5.2 to 5.7.

Example 2: CSTR Reactor Startup Method for *Acetobacterium woodii*

A synthesis gas containing $CO_2$ and $H_2$, was continuously introduced into a stirred tank bioreactor containing *Acetobacterium woodii*, along with a liquid medium containing vitamins, trace metals, cysteine (as sulfur source), and salts as described herein.

A New Brunswick Bioflow 310 reactor containing the fermentation medium was started with actively growing *Acctobacterium woodii*. The rate of agitation of the reactor was set to 200 rpm. This agitation rate was increased throughout the experiment from 200 to 600 rpm. Feed gas flow to the reactor was increased from an initial at 49 mL/min to 137 mL/min. Temperature in the bioreactor was maintained, at 33.5° C. throughout the experiment. Samples of syngas feed into the bioreactor and off-gas from the bioreactor and fermentation broth in the bioreactor were taken at intervals, for example feed gas, off-gas and fermentation broth were sampled about daily, once two hours and once four hours respectively. Above samples were analyzed for consumption or production of various gas components, broth acetic acid concentration, and the optical density (cell density) of the culture. The unaroused volume of the reactor was maintained between 1600 to 1750 ml throughout the experiment. Also the gas flow to the reactor was measured in real time by the mass flow controller regulating syngas to the reactor. The feed syngas composition was 70% $H_2$, 25% CO2 and 5% N2. This experiment was concluded when stable operation was reached.

A cell recycle system (CRS) was attached to the reactor before the start of the experiment. During the experiment, the rate of flow of nutrients (growth medium) to the reactor was as indicated in the Table. Medium feed rate was maintained throughout the experiment. The base (NaOH) feed rate for pH control was 0.14-0.44 ml/min, and through the CRS, 5.1-5.4 ml/min permeate was drawn out from the reactor.

$H_2$ and $CO_2$ in the feed gas was fixed into cell material and acetic acid. The removal of $H_2$ and $CO_2$ was calculated by comparing inlet gas composition with the effluent gas composition. Component gas uptake is expressed in % of gas molecules converted by bacteria. In this experiment the following conversions were achieved; $H_2$: 40%-54%, $CO_2$: 28%-70%. In this experiment the rate of acetic acid production was 5-23 g/l/day.

Results can be summarized as follows:

| | |
|---|---|
| Specific CO2 uptake (mmol $CO_2$/min/gram dry cells) | 0.17-0.33 |
| Specific H2 uptake (mmol $H_2$/min/gram dry cells) | 0.20-0.9 |
| Acetic Acid productivity (g/L/day) | 5-23 |
| Specific Acetic Acid productivity (g/L/day/gCells) | 4.6-11.6 |
| Average Cell Density (g/L) | 1.5 |

Example 3: Fermentation of $CO_2$, CO and $H_2$ by *Acetobacterium woodii*

A gas containing $CO_2$ and $H_2$ was continuously introduced into a stirred tank bioreactor containing *Acetobacterium woodii*, along with a conventional liquid medium containing vitamins, trace metals, and salts. Fermentations were started as described in Example 2 and then continued to stable operation. Mediums and process conditions are described in Example 2. In this Example, the feed gas included 5 mole % CO.

Figure 3:
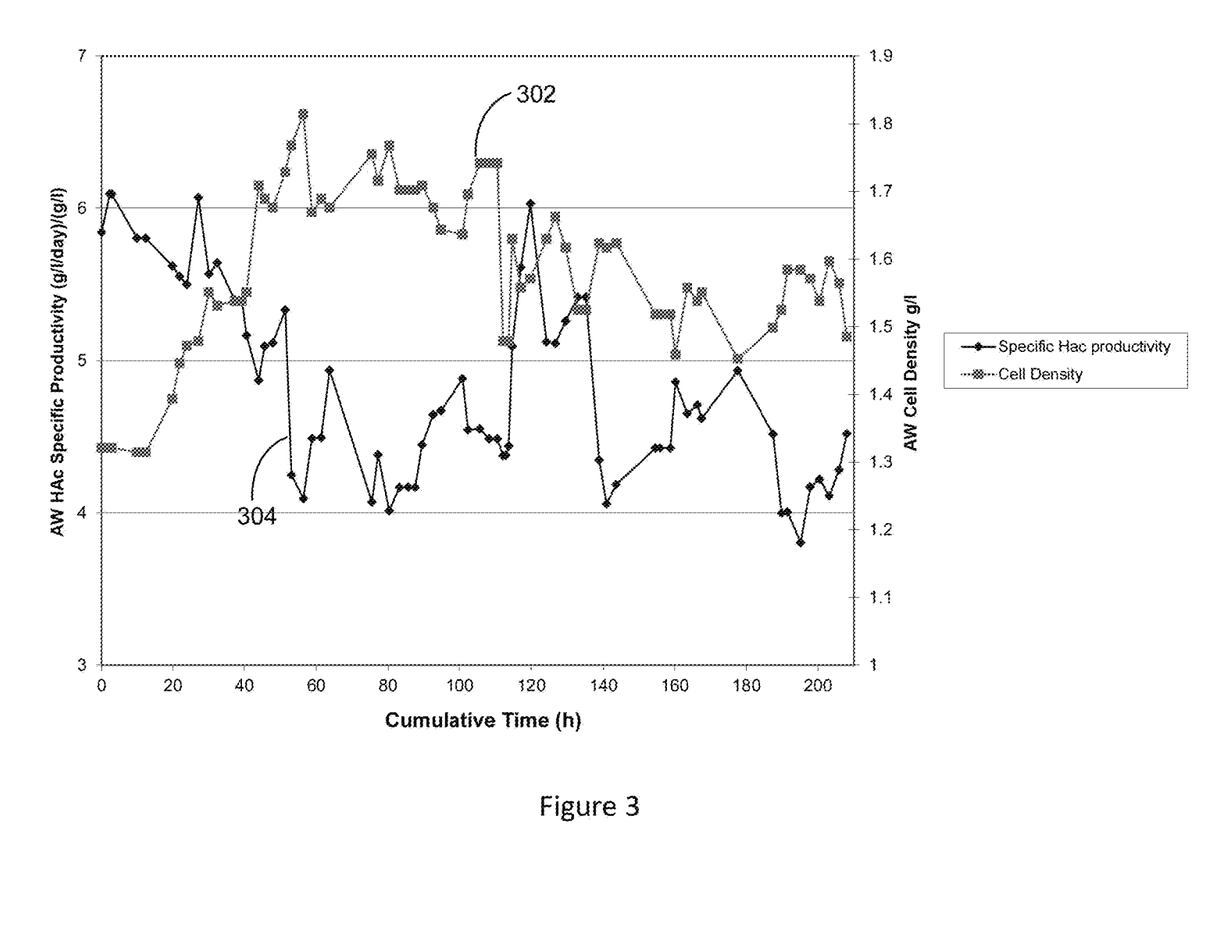
FIG. 3 describes growth of *Acetobacterium woodii* in the presence of 5% CO.
Figure 4:
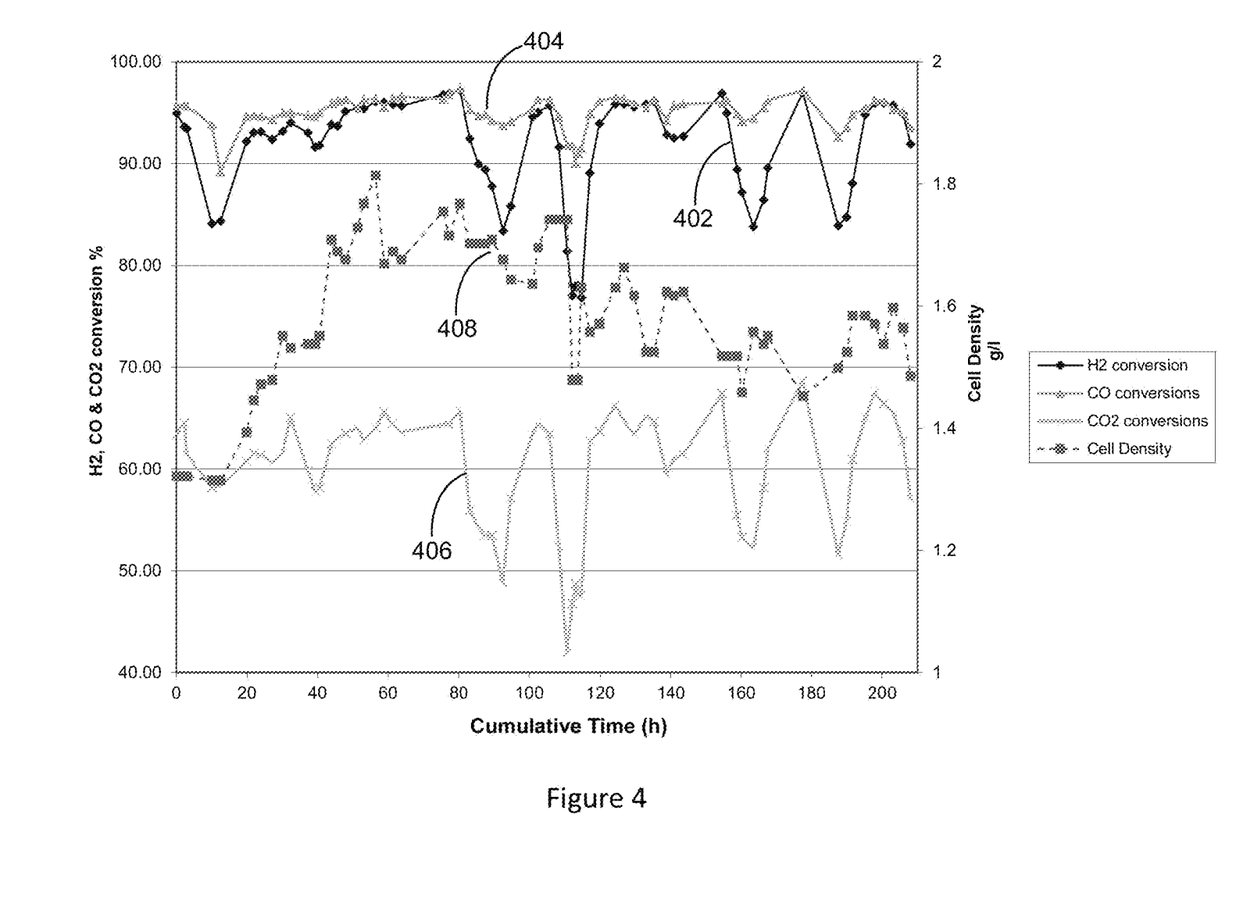
FIG. 4 describes growth of *Acetobacterium woodii* in the presence of 5% CO.

FIG. 3 and FIG. 4 describe growth of *Acetobacterium woodii* in the presence of 5% CO. FIG. 3 illustrates cell density 302 and specific acetic acid productivity 304 versus time. FIG. 4 illustrates $H_2$ conversion 402, CO conversions 404, $CO_2$, conversions 406, and cell density 408.

Example 4: Growth and Maintenance of *Acetobacterium woodii* Culture at pH 5.2 without a Chelating Agent (EDTA) in the Growth Medium A gas stream containing $CO_2$ and $H_2$ was continuously introduced into a stirred tank bioreactor containing *Acetobacterium Woodii*, along with a growth medium as described herein.

A New Brunswick Bioflow 115 reactor containing fermentation medium was started with actively growing *Acetobacterium woodii* (AW). The rate of agitation of the reactor was set to 600 rpm. This agitation rate remained constant throughout the experiment. Feed gas flow to the reactor was maintained at 36.6 mL/min to 44.4 mL/min. Temperature in the bioreactor was maintained at 33° C. throughout the experiment. Na+ levels were kept at 3500 to 4000 ppm. Samples of gas feed into the bioreactor and off-gas from the bioreactor and fermentation broth in the bioreactor were taken at intervals, for example feed gas, off-gas and fermentation broth was sampled about daily, once two hours and once four hours respectively. Above samples were analyzed for consumption or production of various gas components, broth acetic acid concentration, and the optical density (cell density) of the culture. The unaroused volume of the reactor was maintained between 1900 to 2275 ml throughout the experiment. Also the gas flow to the reactor was measured real time by the mass flow controller regulating syngas to the reactor. The feed syngas composition of this experiment was 70% $H_2$, 25% $CO_2$, and 5% $N_2$.

A cell recycle system (CRS) was attached to the reactor before the start of the experiment. During the experiment, the rate of flow of nutrients (growth medium) to the reactor was maintained at 2.8 ml/min. Medium feed rate was maintained throughout the experiment. The average rate of base (NaOH) requirement to maintain pH at 5.2 was 0.075 ml/min, and through the CRS, 2.9 ml/min permeate was drawn out from the reactor.

$H_2$ and $CO_2$ in the feed gas was fixed into cell material and acetic acid. The removal of $H_2$ and $CO_2$ was calculated by comparing inlet gas composition with the effluent gas composition. Component gas uptake can be expressed in % of gas molecules converted by bacteria.

Figure 5:
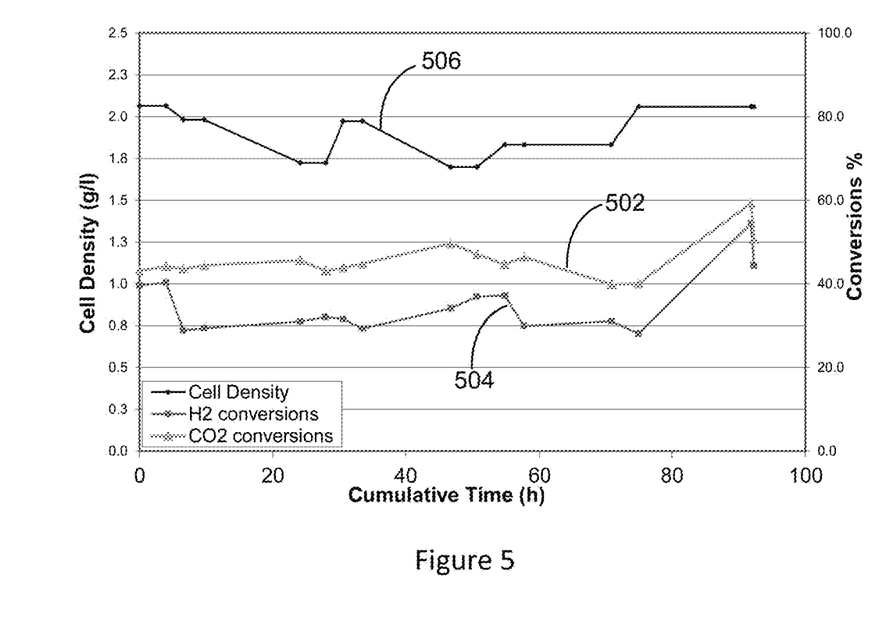
FIG. 5 illustrates $CO_2$, conversions, $H_2$ conversions and cell density of *Acetobacterium woodii* at pH 5.2 without a chelating agent (EDTA) in the growth medium.

The following conversions were achieved:
$H_2$: 28% to 54%
$CO_2$: 40% to 59%
The rate of acetic acid production was 0.7949 (g/L/day)
Average cell density of the culture was 1.9 g/L
$CO_2$ conversions 502, $H_2$ conversions 504 and cell density 506 are shown in FIG. 5.

Example 5: Use of EDDA in Growth Medium

Figure 6:
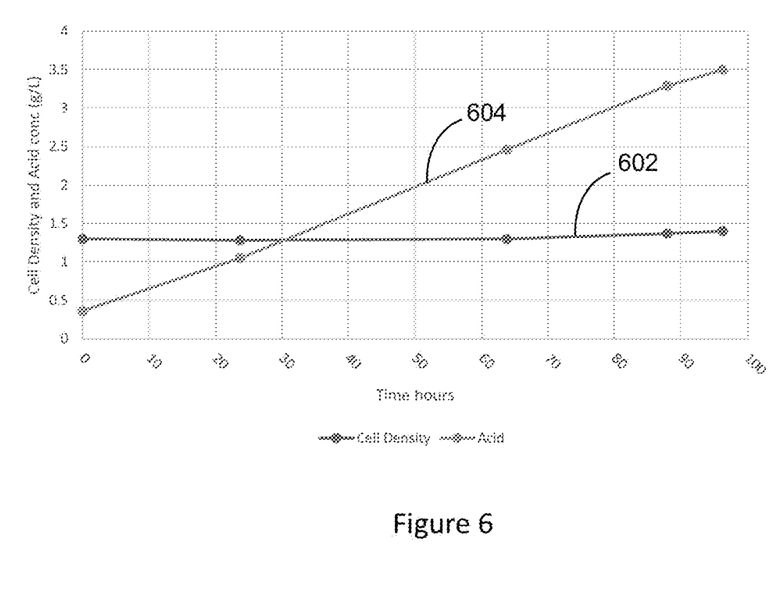
FIG. 6 describes growth of *Acetobacterium woodii* using ethylenediamine diacetic acid (EDDA) as a chelating (complexing) agent in the growth medium.

Fermentations were started as described in Example 2 and included the use of ethylenediamine diatetic acid (EDDA) as a chelating (complexing) agent. Chelating agents are employed to keep metals in solution as the solubility of some of the metals employed in AW medium decreases with the increasing pH. If the pH of the reactor broth is above pH 5.2, chelating agents are employed to provide sufficient amounts of nutrients to AW. FIG. 6 shows a representative 96 hr period of the experiment that illustrates the ability to maintain cell density 602 while producing increasing concentrations of acetic acid 604.

Example 6: Effect of Molybdenum Removal and Re-Addition on Cell Metabolism

Fermentations were started as described in Example 2 and then continued to stable operation. Molybdenum was removed from growth media and then re-added to the growth medium after acetic acid productivity had dropped to 75% of its starting concentration.

Figure 7:
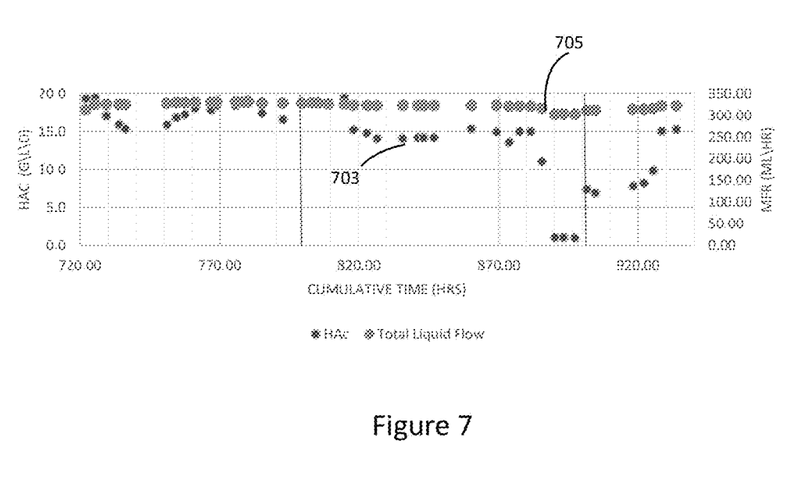
FIG. 7 illustrates the effect of molybdenum on acetic acid production by *Acetobacterium woodii*.

FIG. 7 illustrates acetic acid productivity 703 plotted against its media flow rate 705 with the vertical lines indicating the removal and re-addition of molybdenum to the growth medium. Starting at about 810 cumulative hours, a downward trend of HAc was observed with the molybdenum removal occurring at about 795 cumulative hours. This downward trend decreased, plateaued and then was reversed into an upward trend in correspondence with the re-addition of molybdenum to the media at about 900 hours.

Figure 8:
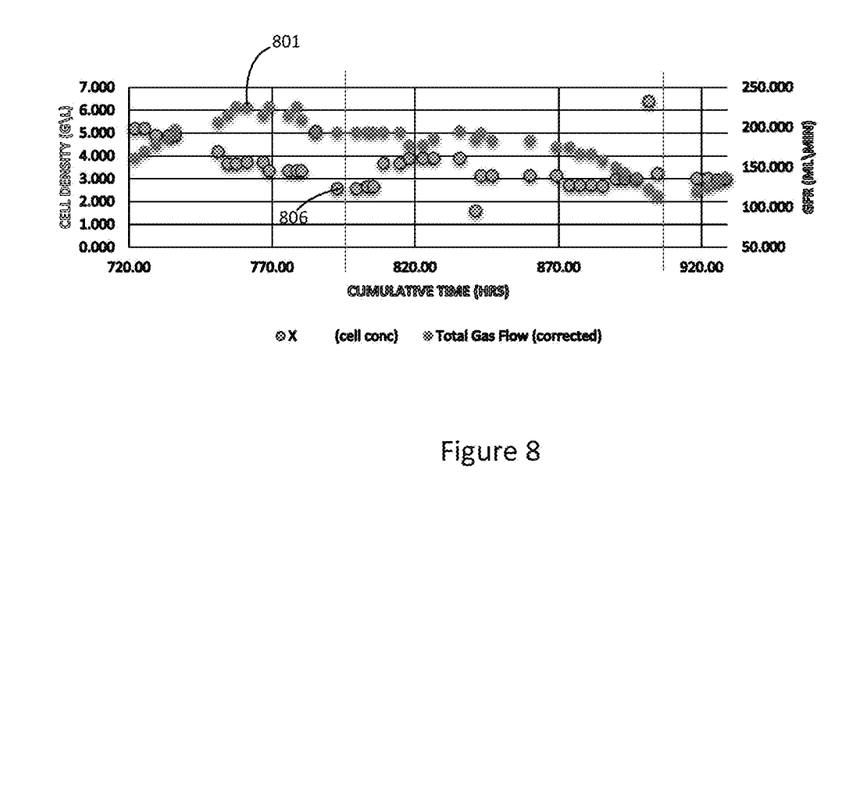
FIG. 8 illustrates the effect of molybdenum on gas flow rate requirement and cell density of *Acetobacterium woodii*.

FIG. 8 illustrates cell density 801 and gas flow rate (GFR) 806 plotted against time with the vertical lines indicating the removal and re-addition of molybdenum to the growth medium. Starting at about 840 cumulative hours, the required GFR was reduced with the molybdenum removal occurring at about 795 cumulative hours. This downward trend was reversed into an upward trend in correspondence with the return of molybdenum to the media at about 900 hours.

While the disclosure herein disclosed has been described by means of specific embodiments, examples and applications thereof, numerous modifications and variations could be made thereto by those skilled in the art without departing from the scope of the disclosure set forth in the claims.

What is claimed is:

1. A process comprising:
providing a gaseous substrate to a bioreactor, the gaseous substrate comprising $CO_2$ and containing about 5 to about 90 mole % $CO_2$, and about 0 to about 5 mole % CO;
providing acetogenic bacteria to the bioreactor;
providing sodium ions to the bioreactor through one or more sodium ion sources; and fermenting the gaseous substrate with the acetogenic bacteria in a fermentation broth comprising the acetogenic bacteria and the one or more sodium ion sources to produce one or more organic acids;

wherein the acetogenic bacteria includes a sodium translocating ATPase that is active during fermentation in the bioreactor, wherein the fermentation broth includes less than about 0.01 grams per liter yeast extract, and less than about 0.01 grams per liter carbohydrate, wherein the sodium ions are provided with a sodium feed rate of about 290 to about 8750 µg/gram of cells/minute, wherein the fermentation broth is maintained at a pH in a range of about 4 to about 6.9, wherein the process provides a $CO_2$ conversion of about 75% to about 100%, and wherein the process provides a specific organic acid productivity of about 10 to about 50 grams organic acid/day/gram of cells.

2. The process of claim 1, wherein the $CO_2$ containing gaseous substrate is selected from the group consisting of industrial gases, fermentor gas streams and mixtures thereof.

3. The process of claim 1, wherein the acetogenic bacteria is selected from the group consisting of *Acetobacterium* bacteria, *Acetogenium kivui, Acetoanaerobium noterae, Acetobacterium woodii, Moorella thermoacetica, Moorella thermoautotrophica, Ruminococcus productus*, and combinations thereof.

4. The process of claim 3, wherein the acetogenic bacteria is *Acetobacterium* woodii.

5. The process of claim 1, wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

6. The process of claim 1, wherein the organic acid is one or more C1 to C10 organic acid.

7. The process of claim 6, wherein the organic acid is acetic acid, butyric acid, or mixtures thereof.

8. A process comprising:
providing a gaseous substrate to a bioreactor, the gaseous substrate comprising and $CO_2$ and $H_2$ and containing about 5 to about 90 mole % $CO_2$, and about 0 to about 5 mole % CO;

providing acetogenic bacteria to the bioreactor;

providing sodium ions to the bioreactor through one or more sodium ion sources; and fermenting the gaseous substrate with the acetogenic bacteria in a fermentation broth comprising the acetogenic bacteria and the one or more sodium ion sources to produce one or more organic acids;

wherein the acetogenic bacteria includes a sodium translocating ATPase that is active during fermentation in the bioreactor, wherein the fermentation broth includes less than about 0.01 grams per liter yeast extract, less than about 0.01 grams per liter carbohydrate, wherein the sodium ions are provided with a sodium feed rate of about 290 to about 8750 µg/gram of cells/minute, wherein the fermentation broth is maintained at a pH in a range of about 4 to about 6.9, wherein the process provides a $CO_2$ conversion of about 75% to about 100%, and wherein the process provides a specific organic acid productivity of about 10 to about 50 grams organic acid/day/gram of cells.

9. The process of claim 8, wherein the gaseous substrate is selected from the group consisting of industrial gases, fermentor gas streams and mixtures thereof.

10. The process of claim 8, wherein the acetogenic bacteria is selected from the group consisting of *Acetobacterium* bacteria, *Acetogenium kivui, Acetoanaerobium noterae, Acetobacterium woodii, Moorella thermoacetica, Moorella thermoautotrophica, Ruminococcus products*, and combinations thereof.

11. The process of claim 10, wherein the acetogenic bacteria is *Acetobacterium woodii*.

12. The process of claim 8, wherein the sodium ion source is provided by a compound selected from the group consisting of sodium chloride, sodium hydroxide, sodium phosphate, sodium sulfate, sodium nitrate, sodium bicarbonate, sodium bisulfate and mixtures thereof.

13. The process of claim 8, wherein the organic acid is one or more C1 to C10 organic acid.

14. The process of claim 13, wherein the organic acid is acetic acid, butyric acid, or mixtures thereof.

* * * * *